(12) United States Patent
Lawson et al.

(10) Patent No.: US 10,182,950 B2
(45) Date of Patent: Jan. 22, 2019

(54) ABSORBENT ARTICLE HAVING IMPROVED SOFTNESS

(75) Inventors: Kathleen Marie Lawson, West Chester, OH (US); Harald Hermann Hundorf, Bonn (DE); Holger Beruda, Schwalbach (DE); Horst Blessing, Cincinnati, OH (US); Peter Dziezok, Hochheim (DE); Axel Krause, Erfstadt (DE); Mattias Schmidt, Idstein (DE); Lutz Stelzig, Frankfurt am Main (DE)

(73) Assignee: The Procter & Gamble Company, Cincinnati, OH (US)

(*) Notice: Subject to any disclaimer, the term of this patent is extended or adjusted under 35 U.S.C. 154(b) by 908 days.

(21) Appl. No.: 12/182,386

(22) Filed: Jul. 30, 2008

(65) Prior Publication Data

US 2009/0118689 A1    May 7, 2009

Related U.S. Application Data

(60) Provisional application No. 60/986,153, filed on Nov. 7, 2007.

(51) Int. Cl.
| | |
|---|---|
| *A61F 13/15* | (2006.01) |
| *A61F 13/532* | (2006.01) |
| *A61F 13/514* | (2006.01) |

(52) U.S. Cl.
CPC .... *A61F 13/5323* (2013.01); *A61F 13/51401* (2013.01); *A61F 13/51405* (2013.01)

(58) Field of Classification Search
CPC .......... A61F 13/51401; A61F 13/51405; A61F 13/5323

USPC .......... 604/358, 366, 368, 370, 378, 385.01, 604/385.23
See application file for complete search history.

(56) References Cited

U.S. PATENT DOCUMENTS

| | | |
|---|---|---|
| 3,860,003 A | 1/1975 | Buell |
| 4,940,464 A | 7/1990 | Van Gompel et al. |
| 5,037,416 A | 8/1991 | Allen et al. |
| 5,092,861 A | 3/1992 | Nomura et al. |
| 5,151,092 A | 9/1992 | Buell et al. |
| 5,246,433 A | 9/1993 | Hasse |
| 5,269,775 A | 12/1993 | Freeland et al. |
| 5,554,145 A | 9/1996 | Roe et al. |
| 5,569,234 A | 10/1996 | Buell et al. |
| 5,571,096 A | 11/1996 | Dobrin et al. |
| 5,607,760 A | 3/1997 | Roe |
| 5,635,191 A | 6/1997 | Roe et al. |
| 5,643,588 A | 7/1997 | Roe et al. |
| 5,788,684 A * | 8/1998 | Abuto et al. .................. 604/368 |

(Continued)

FOREIGN PATENT DOCUMENTS

| | | |
|---|---|---|
| EP | 0 203 289 A2 | 12/1986 |
| EP | 0 780 325 A1 | 6/1997 |

(Continued)

OTHER PUBLICATIONS

International Search Report and Written Opinion, dated Mar. 3, 2009, PCT/IB2008/054593.

*Primary Examiner* — Bradley H Philips
(74) *Attorney, Agent, or Firm* — Andrew J. Hagerty; Sarah M. DeCristofaro (57) ABSTRACT

Disposable absorbent article comprising a chassis comprising a topsheet, a backsheet, and an absorbent core wherein the article has improved softness.

20 Claims, 4 Drawing Sheets

(56) References Cited

U.S. PATENT DOCUMENTS

| | | | |
|---|---|---|---|
| 5,897,545 A | 4/1999 | Kline et al. | |
| 5,957,908 A | 9/1999 | Kline et al. | |
| 6,004,306 A | 12/1999 | Robles et al. | |
| 6,120,487 A | 9/2000 | Ashton | |
| 6,120,489 A | 9/2000 | Johnson et al. | |
| 6,632,385 B2 * | 10/2003 | Kauschke et al. | 264/103 |
| 6,645,569 B2 | 11/2003 | Cramer et al. | |
| 6,803,103 B2 | 10/2004 | Kauschke et al. | |
| 6,861,571 B1 | 3/2005 | Roe et al. | |
| 6,863,933 B2 | 3/2005 | Cramer et al. | |
| 7,112,621 B2 | 9/2006 | Rohrbaugh et al. | |
| 7,744,576 B2 * | 6/2010 | Busam et al. | 604/385.101 |
| 2002/0117419 A1 | 8/2002 | Tippey et al. | |
| 2002/0143304 A1 | 10/2002 | Elder et al. | |
| 2003/0077307 A1 | 4/2003 | Klofta et al. | |
| 2003/0148684 A1 | 8/2003 | Cramer et al. | |
| 2003/0233082 A1 | 12/2003 | Kline et al. | |
| 2004/0131820 A1 * | 7/2004 | Turner | A44B 18/0011 428/92 |
| 2004/0158212 A1 | 8/2004 | Ponomarenko et al. | |
| 2004/0162536 A1 | 8/2004 | Becker et al. | |
| 2004/0167486 A1 | 8/2004 | Busam et al. | |
| 2004/0175343 A1 | 9/2004 | Osborne et al. | |
| 2005/0008839 A1 | 1/2005 | Cramer et al. | |
| 2005/0159720 A1 | 7/2005 | Gentilcore et al. | |
| 2005/0164584 A1 * | 7/2005 | Baratian et al. | 442/329 |
| 2006/0057921 A1 | 3/2006 | Turi et al. | |
| 2007/0118087 A1 * | 5/2007 | Flohr et al. | 604/372 |
| 2007/0156108 A1 * | 7/2007 | Becker et al. | 604/372 |
| 2007/0167928 A1 * | 7/2007 | Becker et al. | 604/366 |
| 2008/0312617 A1 * | 12/2008 | Hundorf et al. | 604/366 |
| 2008/0312618 A1 * | 12/2008 | Hundorf et al. | 604/366 |
| 2008/0312619 A1 * | 12/2008 | Ashton et al. | 604/366 |
| 2008/0312620 A1 * | 12/2008 | Ashton et al. | 604/366 |
| 2008/0312621 A1 * | 12/2008 | Hundorf et al. | 604/366 |
| 2008/0312622 A1 * | 12/2008 | Hundorf et al. | 604/366 |
| 2008/0312623 A1 * | 12/2008 | Hundorf et al. | 604/366 |
| 2008/0312624 A1 * | 12/2008 | Hundorf et al. | 604/366 |
| 2008/0312625 A1 * | 12/2008 | Hundorf et al. | 604/367 |
| 2008/0312628 A1 * | 12/2008 | Hundorf et al. | 604/378 |

FOREIGN PATENT DOCUMENTS

| | | |
|---|---|---|
| EP | 1088537 A2 | 4/2001 |
| JP | 2007097979 A * | 4/2007 |
| WO | WO 95/16746 A1 | 6/1995 |
| WO | WO 98/24391 A2 | 6/1998 |
| WO | WO 00/69481 A1 | 11/2000 |
| WO | WO 02/064877 A2 | 8/2002 |

* cited by examiner

ABSORBENT ARTICLE HAVING IMPROVED SOFTNESS

CROSS REFERENCE TO RELATED APPLICATIONS

This application claims the benefit of U.S. Provisional Application No. 60/986,153, filed on Nov. 7, 2007.

FIELD OF THE INVENTION

The present invention generally relates to an absorbent article, and more particularly to a disposable absorbent article with absorbent particulate polymer material, such as a diaper.

BACKGROUND OF THE INVENTION

Disposable absorbent articles include disposable diapers, disposable feminine hygiene products, and disposable incontinence undergarments. A disposable absorbent article can receive and contain bodily waste while being worn by a wearer. Such articles can be made with various materials in a number of configurations. Multiple attempts have been made to provide them with an overall good fit and with a high absorbent capacity. Modern diapers make use of absorbent materials, which allow for storage of large amounts of liquid in thinner absorbent articles.

U.S. Patent Publication No. 2004/0162536 discloses an absorbent core for an absorbent article that provides an improved immobilization of absorbent polymer material when the article is fully or partially urine loaded. The absorbent core is useful for providing an absorbent article having increased wearing comfort.

U.S. Patent Publication No. 2004/0167486 discloses an absorbent core for an absorbent article that provides increased wearing comfort to the article and makes it thin and dry.

While the aforementioned applications describe an absorbent article having an improved fit and a thinner appearance, a need still exists for a mechanism to provide improved softness to thinner absorbent articles.

SUMMARY OF THE INVENTION

The present invention is directed to a disposable absorbent article comprising a chassis including a topsheet and a backsheet and a substantially cellulose free absorbent core located between the topsheet and the backsheet and including first and second absorbent layers, the first absorbent layer including a first substrate and the second absorbent layer including a second substrate, the first and second absorbent layers further including superabsorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first absorbent layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area. In one embodiment, the backsheet comprises a hydroenhanced nonwoven. In one embodiment, the nonwoven comprises a surface coating. In one embodiment, the backsheet comprises a hydroenhanced nonwoven web having a fiber surface modifying agent on the web. The nonwoven of the present invention may have a basis weight of at least about 22 gsm. The article may have an in-bag compression of less than about 50%.

DETAILED DESCRIPTION OF THE INVENTION

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic adhesive material/composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic adhesive material/composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate 64 and second substrate 72 are separated by a multiplicity of superabsorbent particles. There may be some extraneous superabsorbent particles outside of this area between the first substrate 64 and second substrate 72.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

Embodiments of the present invention include disposable absorbent articles having improved softness. Absorbent cores are becoming increasingly thinner as technology advances, and the overall absorbent article is also becoming thinner. Typically, thicker absorbent articles exhibit both technical and perceived softness benefits as compared to thinner ones. The present invention is directed to thinner absorbent articles that have softness that is parity to thicker absorbent articles. Improved softness of thinner absorbent articles is achieved through mechanisms including, but not limited to, hydroenhanced nonwovens, higher basis weight nonwovens, surface treated nonwovens, and less bag compression. Utilizing the mechanisms described in the present invention provide adequate softness, even when the article comprises a thinner absorbent core.

Figure 1:
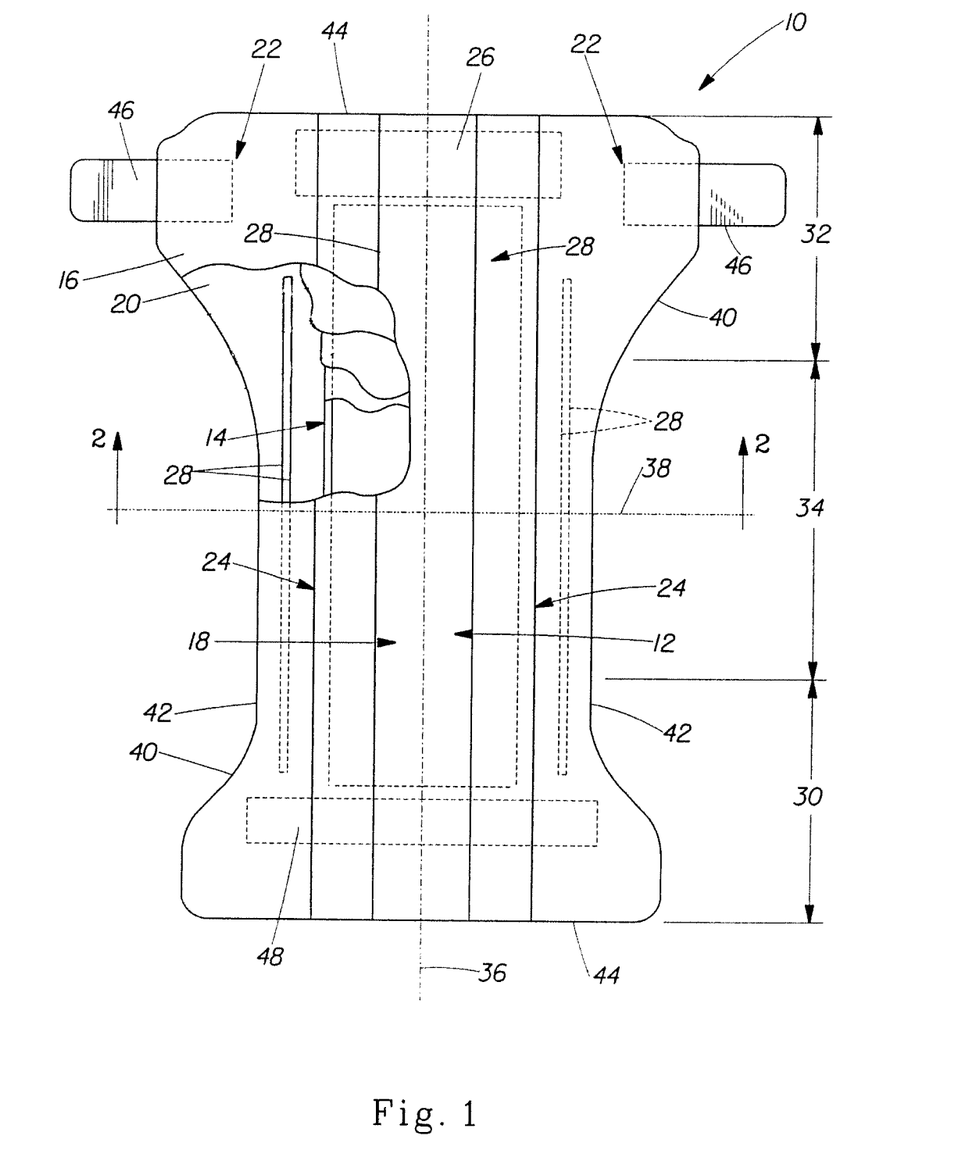
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 10 may also include such other features as are known in the art including front and rear ear panels, waist cap features, elastics and the like to provide better fit, containment and aesthetic characteristics. Such additional features are well known in the art and are e.g., described in U.S. Pat. No. 3,860,003 and U.S. Pat. No. 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. In certain embodiments, the fastening device may comprise cotton or cotton-like materials for additional softness or consumer perception of softness. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 20 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 20 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 20. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g/24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Suitable non-woven materials useful in the present invention include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the nonwovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent applications Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the nonwoven may comprise a material that provides good recovery when external pressure is applied and removed. Further, according to a certain embodiment, the nonwoven may comprise a blend of different fibers selected, for example from the types of polymeric fibers described above. In some embodiments, at least a portion of the fibers may exhibit a spiral-crimp which has a helical shape. In some embodiments, the nonwoven may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

In order to achieve improved softness of the absorbent article, in one embodiment, nonwovens of the present invention are hydroenhanced. Hydroenhanced nonwovens are described in U.S. Pat. No. 6,632,385; U.S. Pat. No. 6,803,103; U.S. Patent Publication No. 2006/0057921.

In order to achieve improved softness of the absorbent article, in a certain embodiment, the nonwoven may be treated by a "selfing" mechanism. By "selfing" nonwovens, high densities of loops (>150 in$^{-2}$) are formed which protrude from the surface of the nonwoven substrate. Since these loops act as small flexible brushes, they create an additional layer of springy loft, which may enhance softness. Nonwovens treated by a selfing mechanism are described in U.S. Patent Application No. US20040131820A1

In order to achieve improved softness of the absorbent article, in one embodiment, nonwovens of the present invention may include a surface coating. In one embodiment, the surface coating may include a fiber surface modifying agent. Preferred fiber surface modifying agents are described in U.S. Pat. No. 6,632,385; U.S. Pat. No. 6,803,103; U.S. Patent Publication No. 2006/0057921.

In order to achieve improved softness of the absorbent article, in a certain embodiment, the surface coating may comprise a surfactant coating. One such surfactant coating is available from Fiberweb, under the Tradename Silastol PST.

Any of the nonwovens described herein may be used for the topsheet, backsheet, or any other portion of the absorbent article comprising a nonwoven. In order to achieve improved softness of the absorbent article, the nonwovens of the present invention may have a basis weight of greater than about 20 gsm, greater than about 22 gsm, greater than about 24 gsm, greater than about 26 gsm, greater than about 28 gsm, greater than about 30 gsm, greater than about 32 gsm.

Figure 2:
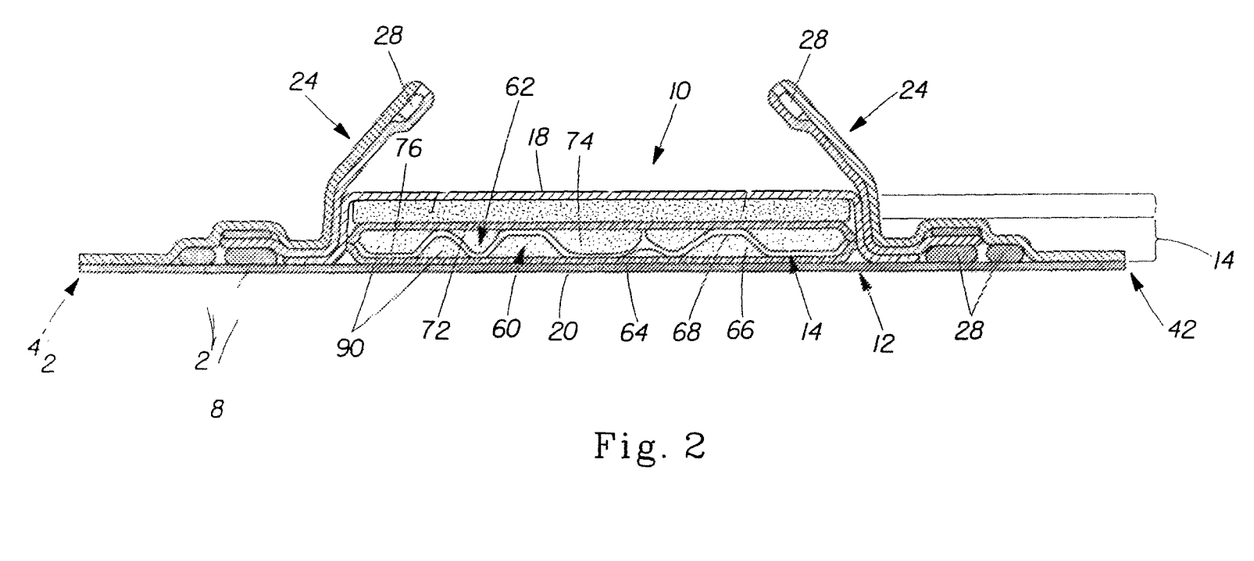
FIG. 2 is a cross sectional view of the diaper shown in FIG. 1 taken along the sectional line 2-2 of FIG. 1.
Figure 3:
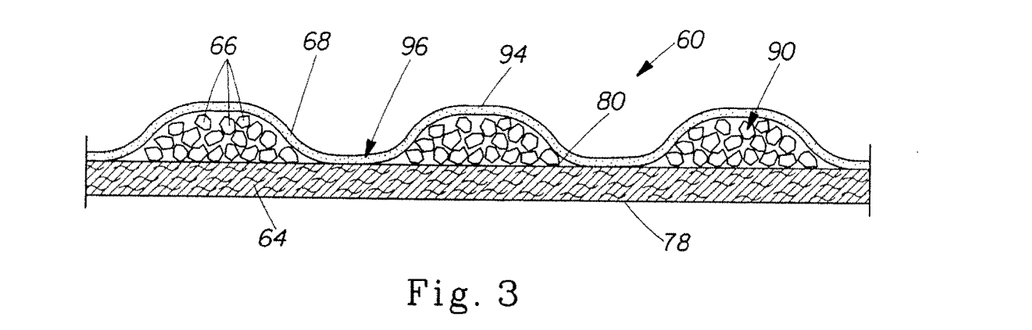
FIG. 3 is a partial cross sectional view of an absorbent core layer in accordance with an embodiment of this invention.
Figure 4:
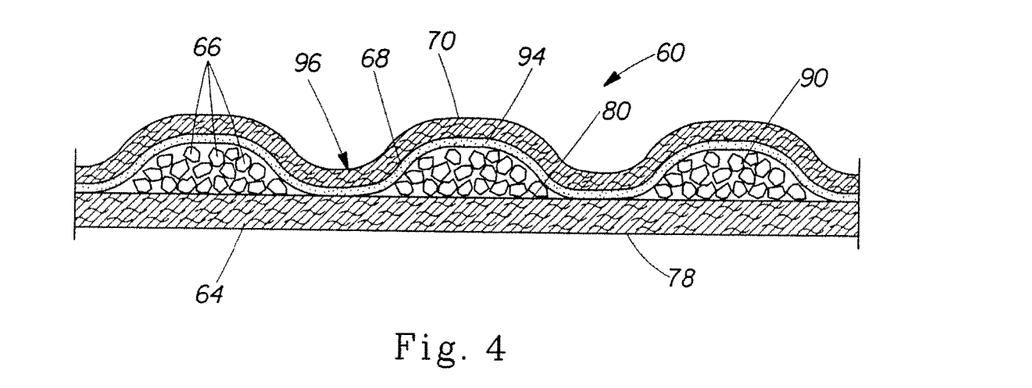
FIG. 4 is a partial cross sectional view of an absorbent core layer in accordance with another embodiment of this invention.

The absorbent core 14 in FIGS. 1-6 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particular polymer material 66 on the substrate 64, and a thermoplastic adhesive material 68 and 76 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic adhesive material 68 and 76.

Likewise, as best illustrated in FIG. 2, the second absorbent layer 62 of the absorbent core 14 may also include a substrate 72, an absorbent particulate polymer material 74 on the second substrate 72, and a thermoplastic adhesive material 68 and 76 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. Likewise, the substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-6, the absorbent particulate polymer material 66 and 74 is deposited on the respective substrates 64 and 72 of the first and second absorbent layers 60 and 62 in clusters 90 of particles to form a grid pattern comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like.

Figure 5:
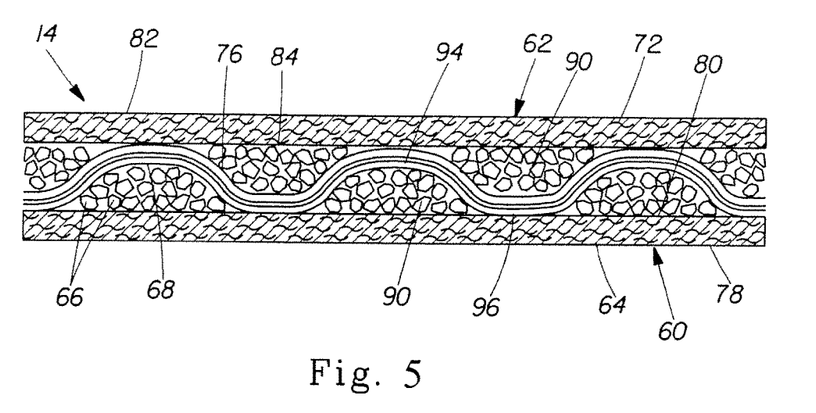
FIG. 5 is a partial sectional view of an absorbent core comprising a combination of the first and second absorbent core layers.
Figure 6:
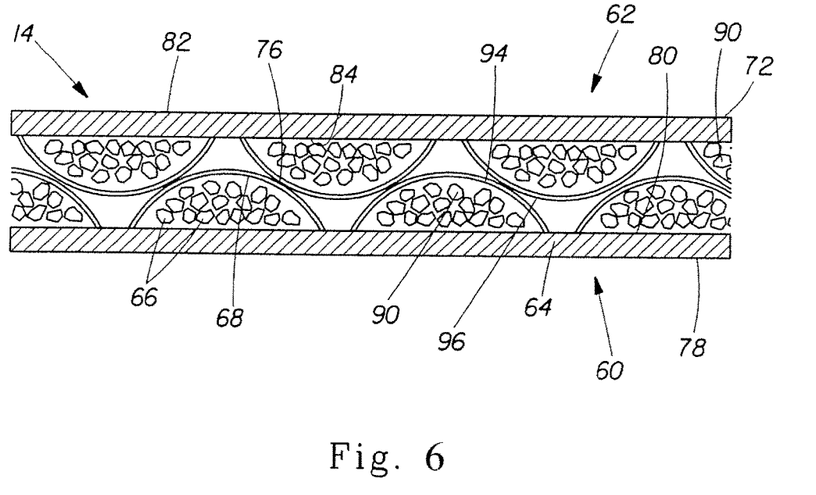
FIG. 6 is a partial sectional view of an absorbent core comprising a combination of the first and second absorbent core layers.

As best seen in FIGS. 5 and 6, the first and second layers 60 and 62 may be combined to form the absorbent core 14. Preferred absorbent articles and cores are described in U.S. patent application Ser. No. 12/141,122; U.S. Publication No. 2004/0167486A1; U.S. Publication No. 2004/0162536A1.

Signal ingredients may be incorporated into one or more components of the absorbent article. Signal ingredients may include, but are not limited to, vitamins A, E, D, and C, panthenol, niacin, omega 3 oils, cocoa butter, beeswax, cashmere, sweet almond oil, jojoba, oatmeal, aloe, cotton, honey, and silk. These signal ingredients may be added to an absorbent article for the purpose of signaling a benefit to the consumer. As an example, one or more of these signal ingredients may be added to a lotion that is applied to an absorbent article component. The signal ingredient alone, or in a lotion, may be applied to the topsheet, backsheet, or any other component of the absorbent article. The lotion may comprise less than about 0.1% by weight, less than about 0.01% by weight, less than about 0.006% by weight, less than about 0.005% by weight, less than about 0.004% by weight, less than about 0.003% by weight, less than about 0.002% by weight, and less than about 0.001% by weight of the signal ingredient.

Additionally, the signal ingredient may, in combination with other absorbent article features, result in an unexpected synergy for communicating a benefit to the consumer. As an example, consumers may respond unexpectedly more favorably to an absorbent article that is thin and soft in combination with a communication that lotion in the diaper comprises vitamin E than they would respond to either communication on its own.

An example of a diaper lotion comprising vitamin E as a signal ingredient may include the following formula:
PET/StOH Mix (ratio=1.41) 94.0% to 99.8% (by weight)
Aloe Extract 0.1% to 3.0% (by weight)
Vitamin E 0.001% to 0.1% (by weight)

Further, vitamin E may be used in its natural form or esters of natural vitamin E may be used (e.g., vitamin E acetate). US Pub Nos. 2002/0143304; 2004/0175343; 200310077307; U.S. Pat. Nos. 5,643,588; 5,635,191; 5,607,760; 6,861,571; and WO Application Nos. 00/69481; and 98/24391 disclose various absorbent article lotions that signal ingredients may be added to.

Another way to achieve improved softness of the absorbent article is through a lower in-bag compression. Lower compression rates result in a softer feeling absorbent article. Preferred in-bag compression percentages of the present invention are less than about 54%, less than about 52%, less than about 50%, less than about 49%, less than about 48%, less than about 47%, less than about 46%. In order to determine in-bag compression percentage, the following test method is used:

I. Determine Free Stack Height

Equipment

Universal Diaper Packaging Tester (UDPT), including a vertical sliding plate for adding weights. It is counterbalanced by a suspended weight to assure that no downward force is added from the vertical sliding plate assembly to the diaper package at all times. The UDPT is available from Matsushita Industry Co. LTD, 7-21-101, Midorigaoka-cho, Ashiya-city, Hyogo JAPAN. Zip code: 659-0014.

A 850 g (±5 g) weight.

Stopwatch with an accuracy to 1 second.

Test Procedure

A) Apparatus Calibration

Pull down the vertical sliding plate until its bottom touches the tester base plate.

Set the digital meter located at the side of the vertical sliding scale to zero mark.

Raise the vertical sliding plate away from the tester base plate.

B) Definitions

Before-bagger free height refers to the free height data measured on 10 pads of fresh diapers.

Fresh Diapers—10 diapers that have never been compressed (stack should be removed (where safely possible) immediately after exit from stacker, before any compression has occurred. If this is not possible, they should be removed from the fingers of a safely stopped stacker chain).

Out-bag free height designates the free height data measured on 10 pads of aged diapers.

Aged Diapers—10 diapers that have been held under compression for approximately 1 minute and/or longer (i.e. 10 diapers come from a freshly opened diaper package).

C) Free Height Measurement

Select 10 adjacent pads of diapers out of the middle from an appropriate source; Fresh diapers for before-bagger free height; Aged diapers for out-of-bag free height.

Neatly stack these 10 pads of diapers underneath the vertical sliding plate. (Align the center of the top pad directly below the central counter sunk hole of the vertical sliding plate.)

Place the 850 g weight onto the vertical sliding plate.

Allow the vertical sliding plate to slide down until its bottom lightly touches desired highest point of the stack.

Measure the stack dimensions in mm by reading the value that appears on the digital meter.

Remove the weight.

Raise the vertical sliding plate away from the stack and remove the stack.

Record the stack height reading to the nearest 1 mm shown on the digital meter.

Procedure—Aging Profile

A) Collect a minimum of three data points from different sample sets. e.g., Measure first point from fresh diapers, e.g., measure second point from diapers being aged in bag for 30 mm/1 hr/6 hr/12 hr/24 hr, e.g., measure third point from diapers being aged in bag for 5 days or longer.

B) Repeat the three steps as described in "Test Procedure" steps A), C), and D).

Procedure—Out-of-Bag Free Height Recovery

A) Collect 10 pads of fresh/aged diapers.

B) Repeat the first two steps as described in "Test Procedure" steps A) and C).

C) Repeat the steps above for general free height measurement except changing the waiting time (i.e., measure first point at 1 min and remaining points at 30 mm/1 hr/6 hr/12 hr/1 day/3 days/5 days, or longer).

Calculation/Reporting

Report Sample Identification, i.e. complete description of product being tested (product brand name/size).

Report the determined value for all measurement to the nearest 1 mm.

NOTE: In case of a series of measurements report the number of tested samples, and calculate/report the Average, Standard deviation, Minimum and Maximum of the values.

Report the Production Date of the measured package (taken from package coding).

Report the Testing Date and Analytical Method used (GCAS).

II. Determine In-Bag Stack

Equipment

Universal Diaper Packaging Tester (UDPT), including a vertical sliding plate for adding weights. It is counterbalanced by a suspended weight to assure that no downward force is added from the vertical sliding plate assembly to the diaper package at all times. The UDPT is available from Matsushita Industry Co. LTD, 7-21-101, Midorigaoka-cho, Ashiya-city, Hyogo JAPAN. Zip code: 659-0014.

A 850 g (±5 g) weight.

Definitions

"Package Width" is defined as the maximum distance between the two highest bulging points along the same compression stack axis of a diaper package.

In-Bag Stack Height=(Package Width I Pad Count Per Stack)×10 pads of diapers,

Apparatus Calibration

Pull down the vertical sliding plate until its bottom touches the tester base plate.

Set the digital meter located at the side of the vertical sliding scale to zero mark.

Raise the vertical sliding plate away from the tester base plate.

Test Procedure

Put one of the side panel of the diaper package along its width standing at the center of the tester base plate. Make sure the horizontal sliding plate is pulled to the right so it does not touch the package being tested.

Add the 850 g weight onto the vertical sliding plate.

Allow the vertical sliding plate to slide down until its bottom lightly touches desired highest point of the package.

Measure the package width in mm (distance from the top of the base plate to the top of the diaper package). Record the reading that appears on the digital meter.

Remove the 850 g weight.

Raise the vertical sliding plate away from the diaper package.

Remove the diaper package.

Calculation/Reporting

Calculate and report the "In-Bag Stack Height"=(Package Width I Pad Count Per Stack)×10.

Report Sample Identification, i.e. complete description of product being tested (product brand name/size).

Report the determined value for each measurement (Length/Width/Front-to-Back) to the nearest 1 mm.

NOTE: In case of a series of measurements report the number of tested samples, and calculate/report the Average, Standard deviation, Minimum and Maximum of the values.

Report the Production Date of the measured package (taken from package coding).

Report the Testing Date and Analytical Method used (GCAS).

III. Calculate %

Calculate %: 1-(In-Bag Stack Height)/(Free Stack Height)=%

All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
a chassis including a topsheet and a backsheet; and
an absorbent core comprising less than 10% by weight of cellulosic fibers, the absorbent core being located between the topsheet and the backsheet and including first and second absorbent layers, the first absorbent layer including a first substrate and the second absorbent layer including a second substrate, the first and second absorbent layers further including superabsorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area;

wherein the backsheet comprises a hydroenhanced nonwoven, wherein the nonwoven comprises a surface coating, and wherein the surface coating is a surfactant.

2. The disposable absorbent article of claim 1, wherein the article is a diaper.

3. The disposable absorbent article of claim 1, wherein the nonwoven has a basis weight of at least about 22 gsm.

4. The disposable absorbent article of claim 1, wherein the nonwoven has a basis weight of at least about 28 gsm.

5. The disposable absorbent article of claim 1, wherein the nonwoven has a basis weight of at least about 30 gsm.

6. The disposable absorbent article of claim 1, wherein the article has an in-bag compression measured as the ratio of an In-Bag stack height to Free stack height of less than about 50%.

7. The disposable absorbent article of claim 1, wherein the article has an in-bag compression measured as the ratio of an In-Bag stack height to Free stack height of less than about 47%.

8. The disposable absorbent article of claim 1, wherein the nonwoven has been treated by selfing.

9. The disposable absorbent article of claim 1, wherein the nonwoven comprises fibers having different degrees of crimp or different types of crimp or both.

10. The disposable absorbent article of claim 1, comprising a signal ingredient applied to the topsheet, the backsheet, or both.

11. The disposable absorbent article of claim 10, wherein the signal ingredient has been applied as a lotion.

12. The disposable absorbent article of claim 1, wherein the backsheet has a water vapor transmission rate of greater than 2000 g/24h/m$^2$.

13. A disposable absorbent article comprising:
a chassis including a topsheet and a backsheet; and
an absorbent core comprising less than 10% by weight of cellulosic fibers, the absorbent core being located between the topsheet and the backsheet and including first and second absorbent layers, the first absorbent layer including a first substrate and the second absorbent layer including a second substrate, the first and second absorbent layers further including superabsorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area;

wherein the backsheet comprises a hydroenhanced nonwoven, wherein the nonwoven comprises a surface coating, wherein the surface coating is a surfactant, and wherein the nonwoven is treated by a selfing mechanism.

14. The disposable absorbent article of claim 13, wherein the topsheet comprises a nonwoven; wherein the nonwoven comprises a treatment selected from the group consisting of application of a fiber surface modifying agent, application of a surfactant, and treatment by a selfing mechanism.

15. A disposable absorbent article comprising:
a chassis including a topsheet and a backsheet; and
an absorbent located between the topsheet and the backsheet and including first and second absorbent layers, the first absorbent layer including a first substrate and the second absorbent layer including a second substrate, the first and second absorbent layers further including superabsorbent particulate polymer material deposited on the first and second substrates and thermoplastic adhesive material covering the absorbent particulate polymer material on the respective first and second substrates, the first and second absorbent layers combined together such that at least a portion of the thermoplastic adhesive material of the first layer contacts at least a portion of the thermoplastic adhesive material of the second absorbent layer, the absorbent particulate polymer material is disposed between the first and second substrates in an absorbent particulate polymer material area, and the absorbent particulate polymer material is substantially continuously distributed across the absorbent particulate polymer material area;

wherein the backsheet comprises a hydroenhanced nonwoven, wherein the nonwoven comprises a surface coating, and wherein the surface coating is a surfactant.

16. The disposable absorbent article of claim 15, wherein the article is a diaper.

17. The disposable absorbent article of claim 15, wherein the nonwoven has a basis weight of at least about 22 gsm.

18. The disposable absorbent article of claim 15, wherein the topsheet comprises a nonwoven; wherein the nonwoven comprises a treatment selected from the group consisting of application of a fiber surface modifying agent, application of a surfactant, and treatment by a selfing mechanism.

19. The disposable absorbent article of claim 15, wherein the nonwoven has been treated by selfing.

20. The disposable absorbent article of claim 15, wherein the nonwoven comprises fibers having different degrees of crimp or different types of crimp or both.

* * * * *